Nov. 25, 1975 C. F. ZAIGER Plant Pat. 3,808
APPLE TREE
Filed Jan. 9, 1975
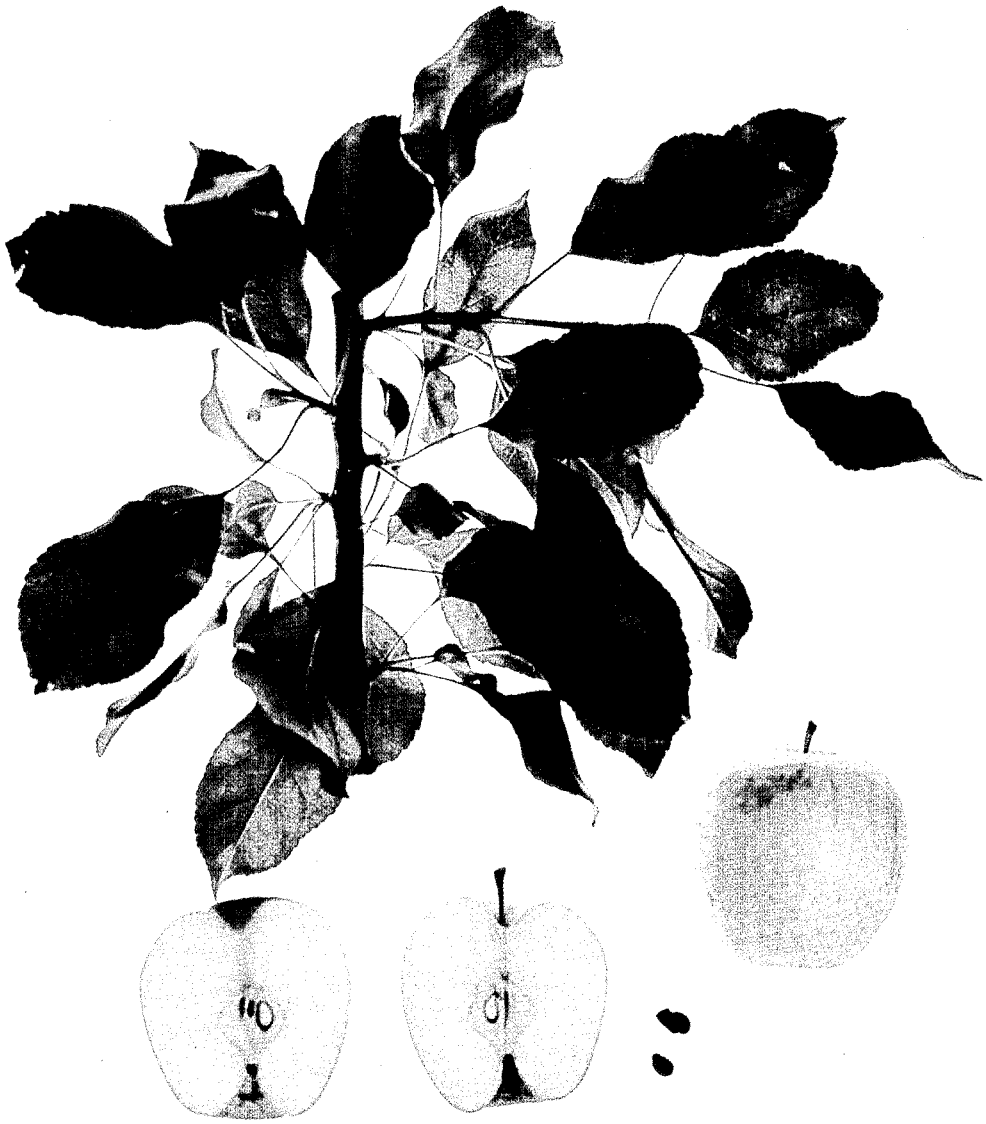

United States Patent

Plant Pat. 3,808
Patented Nov. 25, 1975

3,808
APPLE TREE

Chris Floyd Zaiger, 537 Rosemore Ave.,
Modesto, Calif. 95351

Filed Jan. 9, 1975, Ser. No. 539,767
Int. Cl. A01h *5/03*
U.S. Cl. Plt.—34 1 Claim

ABSTRACT OF THE DISCLOSURE

A variety of apple tree which is of semi-dwarf growth; having a high number of fruit spurs per unit length of wood. The tree being a highly productive and regular bearer of medium size fruit of good keeping, eating and cooking quality.

ORIGIN OF THE VARIETY

The present variety of semi-dwarf apple was originated by me in my experimental orchard located in Modesto, Stanislaus County, Calif., as a selected seedling from a large number of seedlings obtained from Yellow Delicious apple seed that had resulted from open pollinated flowers. These seedlings, which were planted and grown under careful observation by me, gave many and varying characteristics; one such seedling of which is the present variety, having been considered especially desirable with respect to its semi-dwarf growth habit and high quality fruit.

ASEXUAL REPRODUCTION OF THE VARIETY

The present variety of apple tree was asexually reproduced by me—in my said experimental orchard—by budding, and in maturity, such reproductions ran true—in all respects—to the original tree.

SUMMARY OF THE VARIETY

The present variety of apple tree is characterized by its semi-dwarf, upright growth, its large number of spurs per unit of stem length, and by being a highly productive and regular bearer of medium size fruit of good keeping, eating and cooking quality. The flesh is crunchy and firm, the mild aroma, coupled with high sugar content, make this apple particularly desirable for substantially all uses, especially cooking or canning.

BRIEF DESCRIPTION OF THE DRAWING

The drawing is an illustration, by photographic reproduction in color, of a section of branch showing spurring and upper and lower surfaces of leaves; one whole fruit, two halves and three seeds.

DESCRIPTION OF THE VARIETY

The botanical details of the new and distinct variety of apple tree—with color definition (except those in common color terms) referenced to Reinhold Color Atlas by A. Korneruf and J. H. Wanscher—are as follows:

Tree:
- *Size.*—Semi-dwarf—approximately ⅓ to ½ normal size.
- *Vigor.*—Non-vigorous.
- *Growth.*—Upright.
- *Density.*—Dense.
- *Production.*—Very productive.

Trunk:
- *Size.*—Stocky.
- *Texture.*—Medium.

Branches: Medium.
- *Lenticels.*—Medium number. Very slightly raised.

Leaves:
- *Size.*—Abundant and large. Length—3½" to 5½". Width—2¼" to 3".
- *Form.*—Oblong.
- *Margin.*—Serrated.
- *Petiole.*—Length—1¼" to 1¾".
- *Color.*—Top side—Dark green 28F8 to 28F7. Under side—Dark green 29E6 to 29E7.

Flower buds:
- *Size.*—Large.
- *Length.*—Medium.
- *Form.*—Plump.

Flowers:
- *Blooming period.*—Date of first bloom: Mar. 28, 1974. Date of last bloom: Apr. 10, 1974.
- *Color.*—White.

Fruit:
- *Maturity when described.*—Eating ripe, Sept. 15, 1974.
- *Size.*—Average diameter axially, 2 9/16". Average transversely, 2½".
- *Shape.*—Slightly oblong; with ends flattened.
- *Calyx.*—Eye—approximately 3/16" in diameter. Tubes—approximately ½" long and 3/16" in diameter.
- *Core.*—Medium size. Halves, nearly equal. Seed cavity, approximately ⅝" long and ¼" wide. Carpels, usually 5.

Skin:
- *Thickness.*—Medium.
- *Color.*—Semi-glossy, waxen, small evenly spaced dots of light yellowish-green, 30B7, slightly submerged. Ground color, light yellow, 2A5 to 2A6, over entire surface. Slight blush light red 10A5 to 10A6 on most of the fruit, usually nearer the stem end.

Flesh:
- *Texture.*—Firm. Juicy.
- *Ripens.*—Even.
- *Aroma.*—Slight. Pleasant.
- *Flavor.*—Sub-acid.
- *Eating quality.*—Good.
- *Color.*—Yellowish white 2A2.

Seed:
- *Size.*—Average length—⅜". Average width—3/10".
- *Color.*—Light brown 5D4.

Use: Good eating apple. Very good for cooking and canning.

Keeping quality: Very good.

The tree and its fruit herein described may vary in slight detail due to climatic and soil conditions under which this variety may be grown; the present description being of the variety as grown at Modesto, Stanislaus County, Calif.

I claim:

1. A new and distinct variety of semi-dwarf apple tree, as illustrated and described, bearing medium size firm fruit of good eating and cooking quality, having a semi-dwarf growth habit, heavy spurring, and being highly productive.

No references cited.

ROBERT E. BAGWILL, Primary Examiner